United States Patent [19]
Lasco

[11] 3,972,942
[45] Aug. 3, 1976

[54] OXIDATION OF ALLYLACETONE TO 2,5-HEXANEDIONE IN A WATER-CARBON TETRACHLORIDE SOLVENT SYSTEM

[75] Inventor: Ralph H. Lasco, Painesville, Ohio

[73] Assignee: Diamond Shamrock Corporation, Cleveland, Ohio

[22] Filed: Apr. 8, 1974

[21] Appl. No.: 458,474

[52] U.S. Cl. .......................... 260/593 R; 260/597 R
[51] Int. Cl.² ..................... C07C 45/00; C07C 45/04
[58] Field of Search ..................... 260/597 B, 593 R

[56] References Cited
UNITED STATES PATENTS

| | | |
|---|---|---|
| 3,301,905 | 1/1967 | Reimenschneider et al. .... 260/597 B |
| 3,303,020 | 2/1967 | Clement et al. .................. 260/597 B |
| 3,701,810 | 10/1972 | Hasegawa et al. ............... 260/597 B |

FOREIGN PATENTS OR APPLICATIONS

| | | |
|---|---|---|
| 47-11411 | 4/1972 | Japan .............................. 260/597 B |

OTHER PUBLICATIONS

Yamamoto et al., Kogyo Kakaku Yasshi, vol. 71(6), pp. 945–946, (1968).

Smidt et al., Angewante Chem., vol. 71(5), pp. 176–182, (1959).

Primary Examiner—James O. Thomas, Jr.
Assistant Examiner—James H. Reamer
Attorney, Agent, or Firm—Helen P. Brush

[57] ABSTRACT

An economical process is described for the oxidation of allylacetone to 2,5-hexanedione in a solvent system which is a mixture of water and carbon tetrachloride and employing palladium chloride as the oxidation catalyst. High yields of product are obtained with minimal losses of the expensive palladium catalyst.

7 Claims, No Drawings

OXIDATION OF ALLYLACETONE TO 2,5-HEXANEDIONE IN A WATER-CARBON TETRACHLORIDE SOLVENT SYSTEM

BACKGROUND OF THE INVENTION

1. Field of the Invention

This invention relates to a commercial process for the preparation of 2,5-hexanedione, i.e., acetonylacetone, from allylacetone and, more particularly, relates to the oxidation of allylacetone using palladium chloride as a catalyst in the presence of copper chloride and oxygen, whereby high yields of 2,5-hexanedione are prepared with only small losses of the palladium catalyst.

2. Description of the Prior Art 2,5-Hexanedione or acetonylacetone is important as an organic chemical intermediate. Preparation of this compound through various synthesis routes has been reported in the prior art. For example, Adams et al. in J. Am. Chem. Soc., Vol. 72, p. 4368 (1950), describe the synthesis of 2,5-hexanedione by condensing propylene oxide with acetoacetic acid esters to produce alpha-aceto-gamma-valerolactone, which, in turn, is reacted with dilute hydrochloric acid and converted into 5-hydroxy-2-hexanone. To obtain 2,5-hexanedione, the hydroxy-hexanedione product is then oxidized together with sodium dichromate and sulfuric acid. Also, Shenk in Ber., Vol. 77, p. 661 (1944), describes the preparation of 2,5-hexanedione by oxidizing 2,5-dimethylfuran to 3-hexene-2,5-dione, which product is then hydrogenated to produce 2,5-hexanedione. Still further, in U.S. Pat. No. 2,525,672, Heilbron et al. describe the preparation of 2,5-hexanedione by first reacting 1-bromo-2,3-epoxy-butane with monosodium acetylide in liquid ammonia, and then reacting the 3-hexene-5-yn-2-ol product obtained with mercury sulfate in sulfuric acid.

More recently, in Kogyo Kakaku Zasshi, 71, (6), p. 945-6 (1968), as well as in Japanese Patent Publication No. 1972-11411, Takamori Konaka and Sadao Yamamoto have described a simplified, 1-step process for producing good commercial yields of 2,5-hexanedione from allylacetone in a mixed solvent system which is composed of water in combination with either benzene or dimethylformamide. Palladium chloride is employed as the oxidation catalyst in the presence of prescribed amounts of cupric chloride and oxygen. This process is carried out usually at temperatures of 60°-80° C for overall time periods ranging generally from 3 to 12 hours but typically from 7 to 12 hours. Upon completion of the reaction, the 2,5-hexanedione product is reported as being easily recoverable from the reaction mixture and purified. However, from practice of this process, substantial quantities of undesirable byproducts oftentimes are obtained and losses of the expensive palladium chloride catalyst component are found to be substantial.

It has now been found that by conducting the oxidation process in a manner similar to that described in the aforesaid Japanese patent publication, but with the use of a mixed solvent system composed of water and carbon tetrachloride, commercially acceptable yields of 2,5-hexanedione can be conveniently obtained in shorter reaction times and with much reduced losses of the palladium catalyst.

SUMMARY OF THE INVENTION

Accordingly, the present invention relates to an improved process for oxidizing allylacetone (or ALA) in high overall conversions and with high selectivity to 2,5-hexanedione (or HDO), which process is carried out in a mixed solvent system composed of water in combination with carbon tetrachloride. Palladium chloride is utilized as the oxidation catalyst, also using copper chloride and oxygen as reoxidizing agents for the palladium. From practice of this process, palladium losses typically are reduced to about 1-4 cents per pound of the HDO product, based on a palladium chloride cost of $333/pound.

DESCRIPTION OF THE PREFERRED EMBODIMENTS

The oxidation of allylacetone (ALA) to 2,5-hexanedione (HDO) with the secondary oxidation-reduction reactions occurring in the process of the present invention may be represented broadly by the following equations:

1. Oxidation of ALA to HDO:

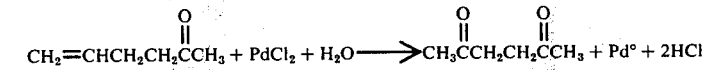

2. Regeneration of palladium to catalytic palladium chloride:

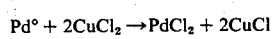

3. Reoxidation of cuprous ion to cupric ion:

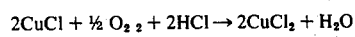

As illustrated in Equation (1) above, the palladium chloride catalyst is reduced to palladium metal during the oxidation of the ALA. The metal is rapidly regenerated for reuse again as catalytic palladium chloride by the oxidizing action of, e.g., cupric chloride, as set forth in Equation (2). In turn, the cuprous chloride formed from the palladium reoxidation step is reoxidized to cupric chloride in the presence of oxygen and hydrochloric acid (Equation 3).

The ALA which is oxidized in the process of this invention is a commercially-available compound which may be synthesized by various methods. For example, it may be synthesized by reacting allyl alcohol and acetone in the presence of an acid-acting catalyst as set forth in U.S. Pat. No. 3,114,772, issued Dec. 17, 1963. Neither the ALA reactant per se nor any particular synthesis method therefor constitute a part of the present invention.

The purity of the ALA is not highly critical for obtaining the desired high yields of product. In general, however, it is desirable to employ ALA which is at least, and preferably, more than 93% pure.

As described previously, palladium chloride is employed herein as the oxidation catalyst in the presence of copper chloride and oxygen as reoxidizing agents therefor. Generally, from about 3 to 150 moles of copper chloride may be employed per each mole of palladium chloride, whereby excellent conversion of ALA with high selectivity to HDO can be obtained in minimum reaction times, likewise with minimal losses of the palladium. In particular, use of from 10–50 moles of copper chloride per mole of palladium chloride gives optimum results and these copper/palladium mole ratios are presently preferred.

The copper chloride requirement itself is supplied by using either cupric chloride ($CuCl_2$) alone or, alternatively, a mixture thereof with cuprous chloride (CuCl). Use of the mixed copper salts has been found to be advantageous for attaining optimum reaction rates. In such instances, the proportion of CuCl employed typically will be less than 50 weight percent of the mixture.

In addition to the aforesaid prescribed copper chloride/palladium chloride ratios (Cu/Pd), it has also been found desirable to employ copper chloride in a sufficient amount to provide a copper to ALA mole ratio (Cu/ALA) which ranges generally between 0.1–10.0, and preferably 0.5–5.0, at least in the initial stages of the oxidation reaction.

As shown in Equation (1) above, hydrochloric acid is produced as a byproduct in the initial oxidation reaction. It has been customary in prior art practice to incorporate additional acid into the reaction to supply sufficient $H^+$ and $Cl^-$ ions for most efficient reoxidation of the palladium. In the process of this invention, however, no additional hydrochloric acid usually needs to be incorporated into the reaction mixture. The pH of the mixture can be easily maintained between 1.0 to 3.0, depending upon the amount of oxygen in the system. It is to be noted that greater yields of product usually will be obtained at a faster rate if no acid is added.

Oxygen may be introduced into the reaction in finely dispersed form at a prescribed rate or the reaction alternatively may be run under oxygen pressure. For example, a satisfactory rate of oxygen feed at atmospheric pressure typically is a minimum of about 2000 cc/min/liter of aqueous oxidant solution. Particularly advantageous results are obtained applying oxygen at a rate of 4000–10,000 cc/min/liter of aqueous oxidant solution. In pressurized reactions, a satisfactory minimum oxygen feed rate is about 50 cc/min/liter of the oxidant solution.

With regard to the solvent system, from 1 to 3 parts carbon tetrachloride, by volume, are advantageously used for each part of water. In turn, from about 2 to about 5 parts of the combined solvent system, by volume, generally are used for each part of ALA reactant.

The process of this invention generally may be carried out at temperatures ranging from 35° to 100° C. For reactions conducted under atmospheric pressure, a suitable reaction temperature is approximately 67° C, i.e., the reflux temperature of the carbon tetrachloride-water azeotrope. Higher reaction temperatures may be attained, of course, by pressurizing the reaction.

Reaction times herein range generally from about 30 minutes to 6 hours, with times ranging from 30 minutes to 3 hours being especially suitable and presently preferred.

According to one embodiment, the process of this invention may be effectively carried out by successively charging prescribed quantities of palladium chloride, copper chloride, water, and carbon tetrachloride together with the total charge of ALA into reactor fitted with an agitator, thermometer, condenser, and oxygen sparger. With continued agitation, oxygen is then introduced into the system and the reaction mixture is heated to the desired temperature. The reaction is continued at this temperature until 80% or more of the ALA has been converted (as determined by analysis of an aliquot sample by vapor phase chromatography).

Alternatively, the process may be conducted by initially charging the prescribed quantities of catalyst and solvent components and only a portion of the ALA reactant into the reactor as described above, while feeding the remaining ALA requirement at a prescribed rate throughout the reaction. In still another method, all of the ALA requirement may be fed incrementally at a prescribed rate throughout the reaction. Further, it is to be understood that any of the various modes for carrying out the process may be conducted efficiently either at atmospheric conditions or under oxygen pressure.

Upon completion of the reaction, whichever operating procedure is employed, the aqueous oxidant layer and the solvent product layer separate cleanly with a sharp interface. The solvent layer, being heavier than the aqueous layer, can be conveniently drawn off from the bottom of the apparatus. The aqueous layer may be extracted several times with solvent to recover small quantities of product present therein. The stripped aqueous layer which contains dissolved palladium catalyst can be recycled and used in a further reaction. The product can be reclaimed from the carbon tetrachloride by solvent stripping.

The amount of palladium lost in the reaction, which amount will be contained in the product stream, can be determined easily by analysis. The palladium loss per reaction usually is in the range of 1–4 cents/pound of product, based on a palladium chloride cost of $333/pound. Under optimum reaction conditions, palladium loss can be less than 1 cent/pound of HDO.

After separation, the catalyst-containing aqueous layer can be recycled to the reactor along with fresh ALA and solvent, and the process thus repeated in a somewhat continuous manner. If semicontinuous operation is desirable, this aqueous oxidant solution need not be stripped of product prior to recycling, as any HDO dissolved therein may be recovered substantially after the next cycle. In practice, it has been found advantageous to recycle the aqueous oxidant solution without product stripping, since small amounts of HDO initially in the reaction mixture appear to accelerate the reaction rate and improve product yields. It is also to be noted that even if present in the reaction mixture at the start of oxidation, the HDO will not react further to more complex derivatives, e.g., triketones, furans, etc., nor will it form chlorinated byproducts.

In order that those skilled in the art may more completely understand the present invention and the preferred methods by which it may be carried out, the following specific examples are given.

EXAMPLE 1

To a 500-cc creased flask equipped with a thermometer, agitator, condenser, bottom take off, and oxygen sparger is added 20.0 g (0.149 mole) cupric chloride, 1.6 g (0.009 mole) palladium chloride, 100 cc water, 150 cc carbon tetrachloride, and 20 cc (0.163 mole) of allylacetone (ALA) assaying 95.5%. The reaction mixture contains a copper chloride:palladium chloride ratio of 17 to 1 and a copper chloride:ALA ratio of 0.91 to 1.

Agitation is started, oxygen feed (200 cc/min) is begun, and the reaction is heated to 67°C. The reaction is continued for 1.8 hours at which time the reaction mixture is sampled and analyzed by vapor phase chromatography. About 94% of the ALA is found to be reacted.

After cooling to room temperature, agitation is stopped. The aqueous oxidant layer and the carbon tetrachloride-HDO layer separate with the organic layer being on the bottom. After draining off the organic layer, the aqueous layer is extracted 4 times with 150 cc carbon tetrachloride to recover the HDO which remains in the aqueous layer. A quantitative analysis by vapor phase chromatography of the main product layer and the combined extracts shows a 94% conversion of ALA with a selectivity of 88%.

The two carbon tetrachloride-HDO solutions are analyzed to determine the palladium content which is found to be 770 micrograms ($\mu$g). There is calculated to be 1283 $\mu$g of palladium chloride present in the product and unavailable for recycling to the reaction. At a palladium chloride cost of $333/pound, this quantity of palladium represents a loss of about 3 cents/pound of HDO.

The HDO product can be recovered by distilling the carbon tetrachloride at atmospheric pressure, followed by vacuum distillation of the residue. 2,5-Hexanedione is a colorless liquid having a boiling point of 73.5°C/15 mm Hg.

EXAMPLE 2

Using the equipment and the general procedure as outlined in Example 1, another experiment is performed using 35 cc. (0.284 mole) of ALA, 53.0 g (0.395 mole) of cupric chloride, and 5.3 g (0.300 mole) of palladium chloride, providing a copper chloride:palladium chloride mole ratio of 13 to 1. The copper chloride:ALA ratio is 1.3 to 1. VPC analysis of the carbon tetrachloride product solution shows 99% of the ALA converted with a selectivity of 71%.

Analysis of the two carbon tetrachloride product solutions for palladium show that the solutions contain 512 $\mu$g of palladium, or the equivalent of 856 $\mu$g of palladium chloride. Based on a palladium chloride cost of $333/pound, this quantity of palladium represents a loss of about 1 cent/pound of HDO.

EXAMPLE 3

For comparison, the experiment of Example 1 was repeated using benzene as the solvent according to the teachings of Japanese Patent Publication No. 1972-11411. After 2 hours of reaction, VPC analysis showed that 95% of the ALA was reacted with a selectivity of 83%.

Analysis of the benzene product layer and the combined benzene extracts showed that the solutions contained 50,100 $\mu$g of palladium or the equivalent of 83,500 $\mu$g of palladium chloride. At a palladium chloride cost of $333/pound, this amount of palladium represents a loss of about 190 cents/pound of HDO.

This palladium loss is significantly greater than realized from the process of this invention as illustrated in Examples 1 and 2 above.

EXAMPLE 4

The process of this invention is conducted somewhat in a semicontinuous manner as follows:

Using the equipment outlined in Example 1, a run is made with repeated recycling of the aqueous solution to the reactor without exhaustive extraction of the HDO after each cycle. The aqueous solution is composed of 20.0 g (0.149 mole) of cupric chloride, 10.0 g (0.100 mole) of cuprous chloride, 0.80 g (0.0453 mole) palladium chloride, 100 cc water, and 5 cc HDO. The copper:palladium ratio is 55 to 1. Twenty cc of ALA (0.163 mole) and 150 cc of carbon tetrachloride are used in each cycle. The copper:ALA ratio is 1.5 to 1. A reaction temperature of 65°–67°C and an oxygen feed of 400 cc/min is used.

At the end of each cycle, the reaction mixture is cooled to 30° C. The carbon tetrachloride layer is then drained from the bottom of the reactor and analyzed for ALA, HDO, and palladium. A fresh charge of ALA and carbon tetrachloride is added to the reactor and the solution heated to reflux again. Results of several cycles are shown below:

TABLE 1

| Cycle | R.T. hrs | ALA Conv. % | HDO Select. % | HDO Yield % | Pd Loss ct./lb HDO |
|---|---|---|---|---|---|
| 1 | 1.3 | 91 | 57 | 52 | 3.9 |
| 2 | 1.7 | 90 | 82 | 74 | 0.5 |
| 3 | 1.8 | 89 | 88 | 78 | 0.1 |
| 4 | 2.1 | 92 | 89 | 82 | 4.3 |
| 5 | 2.5 | 92 | 86 | 79 | 0.6 |
| 6 | 2.0 | 93 | 87 | 81 | 1.1 |
| 7 | 1.5 | 90 | 96 | 86 | 1.8 |
| 8 | 1.5 | 90 | 89 | 80 | 0.7 |
| 9 | 1.7 | 89 | 93 | 83 | 2.0 |
| 10 | 1.7 | 89 | 88 | 78 | 1.8 |

EXAMPLE 5

Another run is made analogous to Example 4. In this case, the aqueous solution is made up using 20.0 g (0.149 mole) cupric chloride, 10.0 g (0.100 mole) cuprous chloride, and 1.6 g (0.0906 mole) palladium chloride dissolved in 100 cc water and 5 cc HDO. Twenty cc of ALA and 150 cc of carbon tetrachloride are fed in each cycle. The copper:palladium ratio is 27 to 1 and the copper:ALA ratio is 1.5 to 1. A reaction temperature of 50°C is used. The results of a number of cycles are shown below:

TABLE 2

| Cycle | R.T. hrs | ALA Conv. % | HDO Select. % | HDO Yield % | Pd Loss ct./lb HDO |
|---|---|---|---|---|---|
| 1 | 2.0 | 96 | 60 | 58 | 4.2 |
| 2 | 1.8 | 90 | 83 | 75 | 1.4 |
| 3 | 1.8 | 91 | 90 | 82 | 1.4 |
| 4 | 1.8 | 93 | 86 | 80 | 0.5 |
| 5 | 2.4 | 94 | 80 | 75 | 0.2 |
| 6 | 2.2 | 89 | 96 | 85 | 0.1 |
| 7 | 2.5 | 89 | 93 | 83 | 2.6 |
| 8 | 2.5 | 92 | 85 | 78 | 2.0 |
| 9 | 2.5 | 88 | 89 | 78 | 0.9 |
| 10 | 2.3 | 89 | 92 | 82 | 1.6 |

What is claimed is:

1. A process for selectively oxidizing allylacetone to 2,5-hexanedione which comprises reacting in a mixed solvent system, at a temperature of 35°–100°C, allylacetone with a palladium chloride catalyst in the presence of copper chloride and oxygen, from 10 to 55 moles of copper chloride being employed per mole of palladium chloride, the quantity of said copper chloride being sufficient to supply from 0.1 to 10.0 moles thereof for each mole of allylacetone wherein the improvement comprises using a mixture containing from 1–3 parts, by volume, carbon tetrachloride per part of water as the solvent system.

2. The process of claim 1 which is conducted for a time period ranging from 30 minutes to 6 hours.

3. The process of claim 1 wherein from 13 to 55 moles of copper chloride are employed per mole of palladium chloride.

4. The process of claim 1 wherein from 0.5 to 5.0 moles of copper chloride are employed per mole of allylacetone.

5. The process of claim 1 wherein the copper chloride requirement is supplied solely by cupric chloride.

6. The process of claim 1 wherein the copper chloride requirement is supplied by a mixture of cupric chloride and cuprous chloride, said cuprous chloride being employed in an amount which is less than 50 percent, by weight of the mixture.

7. The process of claim 1 which is operated in a semicontinuous manner by recycling the catalyst-containing aqueous portion of the solvent system.

* * * * *